United States Patent
Moriya

[11] Patent Number: 6,118,133
[45] Date of Patent: Sep. 12, 2000

[54] APPARATUS AND METHOD FOR OBSERVING DEFECT HAVING MARKS MAKING MEANS

[75] Inventor: Kazuo Moriya, Ageo, Japan

[73] Assignee: Mitsui Mining & Smelting Co., Ltd., Tokyo, Japan

[21] Appl. No.: 09/139,041

[22] Filed: Aug. 24, 1998

[30] Foreign Application Priority Data

Aug. 25, 1997 [JP] Japan ................................ 9-241736

[51] Int. Cl.⁷ ................................................ G01N 21/88
[52] U.S. Cl. .................................. 250/559.45; 250/201.3
[58] Field of Search ........................... 250/559.45, 559.4, 250/201.3, 306, 307; 356/237.1, 237.4, 237.5, 376; 382/149

[56] References Cited

U.S. PATENT DOCUMENTS 5,663,569  9/1997  Hayano ........................ 250/559.45

*Primary Examiner*—Que T. Le
*Attorney, Agent, or Firm*—McEachran, Jambor, Keating, Bock & Kurtz

[57] ABSTRACT

A detect observing apparatus according to the present invention has a purpose for forming an observing specimen by using a TEM and the like in a positive and simple manner and is used in observation of defect or foreign matter in an object to be tested by means of a laser tomography and includes an illumination means for illuminating observing laser light onto the object to be tested, and a microscope for observing the illuminated object to be tested, the apparatus further comprises a marking means for forming marks at a plurality of points on a surface of the object to be tested in the vicinity of the defect or foreign matter to be observed under the microscope, and a position detecting means for detecting positions of the plurality of marks formed on the surface of the object to be tested and a position of the observed defect or foreign matter through the microscope.

8 Claims, 2 Drawing Sheets

APPARATUS AND METHOD FOR OBSERVING DEFECT HAVING MARKS MAKING MEANS

BACKGROUND OF THE INVENTION

1. Field of the Invention

The present invention relates to defect observing apparatus and method for detecting foreign matters and/or defect in an object to be tested such as a crystal body and for obtaining information regarding such defect.

2. Related Background Art

In the past, as a technique for obtaining foreign matters and/or defect in an object to be tested such as a crystal body, there has been proposed a technique in which a position of the defect or scattering intensity is detected by a laser tomography and a specimen for observing the defect by means of a TEM (transmission electron microscope) is formed on the basis of such information and composition or configuration of the defect is ascertained by observing the specimen through the TEM.

However, since the specimen to be observed by the TEM is very thin (for example, having a thickness of several thousand Å, it is very difficult to form the specimen on the basis of the detected position of the defect so that the detected defect is included within the thickness range.

SUMMARY OF THE INVENTION

In consideration of the above-mentioned conventional problem, an object of the present invention is to permit formation of a specimen to be observed by a TEM or the like in a positive and simple manner.

To achieve the above objects, according to the present invention, there is provided a defect observing apparatus used in observation of defect or foreign matter in an object to be tested by means of a laser scattering method and including illumination means for illuminating observing laser light onto an object to be tested, and a microscope for observing the illuminated object to be tested, the apparatus comprising marking means for forming marks at a plurality of points on a surface of the object to be tested in the vicinity of the defect or foreign matter to be observed under the microscope, and position detecting means for detecting positions of the plurality of marks formed on the surface of the object to be tested and a position of the observed defect or foreign matter through the microscope.

The marks formed on the surface of the object to be tested are used as a reference representative of the position of the defect and the like when a thin specimen to be observed by a TEM or the like is formed from the object to be tested. Accordingly, when the specimen is formed, although the defect itself or the foreign matter itself cannot be seen directly, the thin specimen can be formed positively and easily by referring to the marks. That is to say, the marks are formed through an optical system of the defect observing apparatus, and, after the positional relation between the formed marks and the defect and the like is clarified, the thin specimen is formed on the basis of the positional relation.

A defect observing method according to the present invention comprises a marking step for illuminating an observing laser onto an object to be tested, for seeking defect or foreign matter in the illuminated object to be tested by a microscope and for forming marks at a plurality of points on a surface of the object to be tested in the vicinity of the defect or foreign matter to be observed under the microscope, a position detecting step for detecting positions of the plurality of marks obtained by marking and a position of the observed defect or foreign matter through the microscope, a specimen forming step for forming a thin specimen including the defect or foreign matter from the object to be tested, on the basis of a positional relation between the marks and the defect or foreign matter obtained from a detected result, and an observing step for obtaining information regarding the defect or foreign matter by observing the thin specimen. This method can be carried out by using the above-mentioned defect observing apparatus. In this way, the thin specimen can be formed positively and easily.

In a preferred embodiment of the defect observing apparatus of the present invention, the marking means serves to direct marking laser light to an optical axis of the microscope and to form the marks at the plurality of points by the marking laser light through the microscope.

Alternatively, the marking means may form the marks at the plurality of points by using a marker of contact probe type.

Further, there may be provided means for illuminating spot light onto an illuminated position via the microscope in order to previously ascertain the illuminated position, before the marking laser light is illuminated onto the object to be tested in order to form the marks.

The means for illuminating the spot light serves to direct light flux for forming the spot light to the optical axis of the microscope via a dichroic mirror, and the marking means serves to direct the marking laser light to the optical axis of the microscope via the dichroic mirror.

Incidentally, the observing laser light may have a wavelength permeable to the object to be tested, and the marking laser light may have a wavelength absorbed to the surface of the object to be tested. The wavelengths of such laser light may be selected from within a range of 300 to 800 nm.

DETAILED DESCRIPTION OF THE PREFERRED EMBODIMENTS

The present invention will now be explained in connection with a preferred embodiment thereof with reference to the accompanying drawings.

Figure 1:
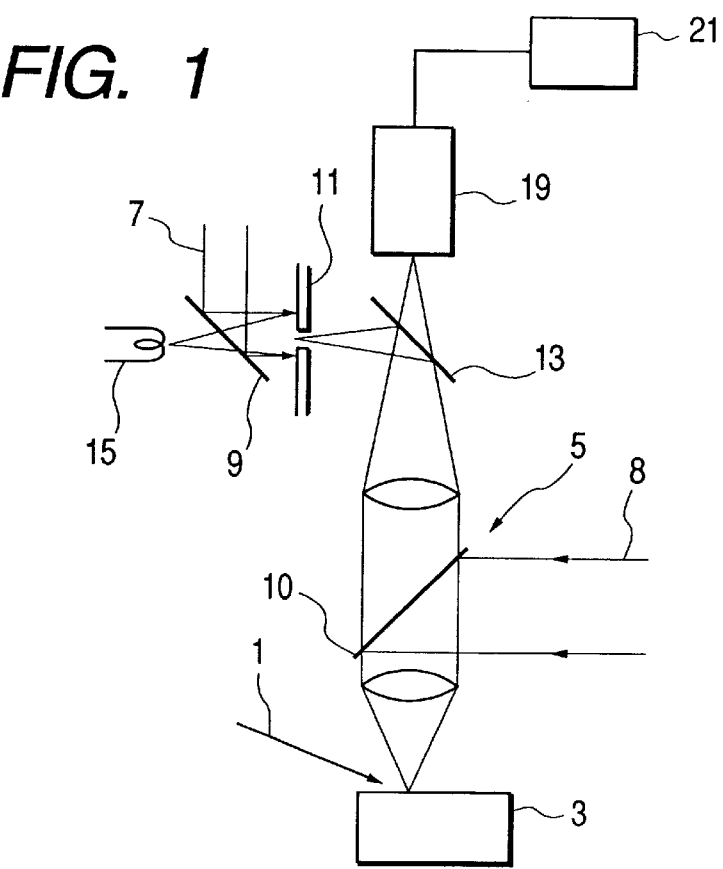
FIG. 1 is a schematic view of a defect observing apparatus using a laser tomography according to a preferred embodiment of the present invention.

FIG. 1 is a schematic view of a defect observing apparatus using a laser tomography according to a preferred embodiment of the present invention. As shown in FIG. 1, the defect observing apparatus comprises illumination means for illuminating an observing laser 1 onto an object 3 to be tested (referred to as "test object" hereinafter), and a microscope 5 for observing the illuminated test object 3 and is adapted to be used in observation of defect or foreign matter in the test object 3. The defect observing apparatus further comprises marking means for forming marks at a plurality of points on a surface of the test object 3 in the vicinity of the defect or foreign matter, when the defect or foreign matter is positioned within a visual field of the microscope 5, and position detecting means for detecting positions of the plurality of marks formed on the surface of the test object 3 by marking and a position of the positioned defect or foreign matter through the microscope 5.

The marking means includes optical means for effecting the marking (forming the mark) at one point on the surface of the test object 3, by directing a marking laser beam 7 to an optical axis of the microscope 5 through a mirror 9, a pinhole 11 and a dichroic mirror 13 and by illuminating the laser beam onto the test object 3 through the microscope 5, and means for shifting the test object 3 in order to effect the marking at a plurality of points.

Figure 2:
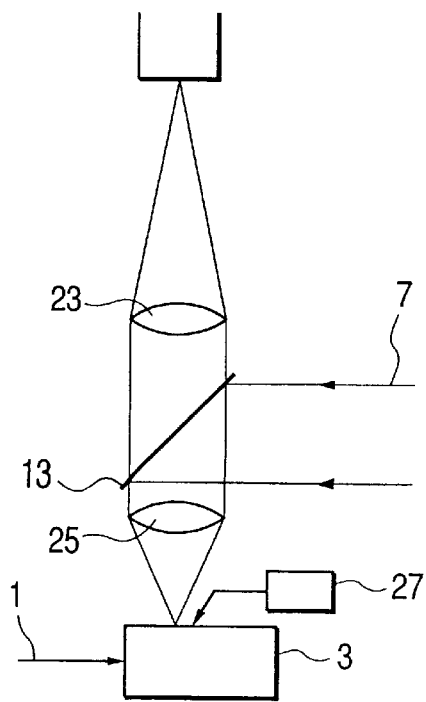
FIG. 2 is a schematic view showing an alteration of the apparatus of FIG. 1.

Incidentally, as shown in FIG. 2, the marking laser beam 7 may be directed to the optical axis of the microscope 5 between an objective lens 25 and an eyepiece 23 of the microscope 5. Further, in place of illumination of the marking laser beam 7, a marker 27 of contact probe type may be used for effecting the marking. Further, the observing laser light 1 may be illuminated from a side of the test object 3.

The position detecting means includes means for directing mark illuminating light flux 8 to the optical axis of the microscope 5 through a half mirror 10 and for illuminating the mark on the test object 3 through the microscope 5, a TV camera 19 for imaging the illuminated mark and the defect and the like in the test object 3 illuminated by the observing laser light 1 through the microscope 5 and for converting the imaged matters into image data, and an information processing means 21 for identifying the positions of the imaged mark and defect and the like on the basis of the image data.

Further, the defect observing apparatus includes a means for illuminating spot light onto an illuminated position via the microscope 5 in order to previously ascertaining the illuminated position, before the marking laser beam 7 is illuminated onto the test object 3 in order to form the mark. The spot light illuminating means serves to form the spot light by directing light 17 from a spot light forming light source 15 to the optical axis of the microscope 5 through the pinhole 11 and the dichroic mirror 13.

Figure 3:
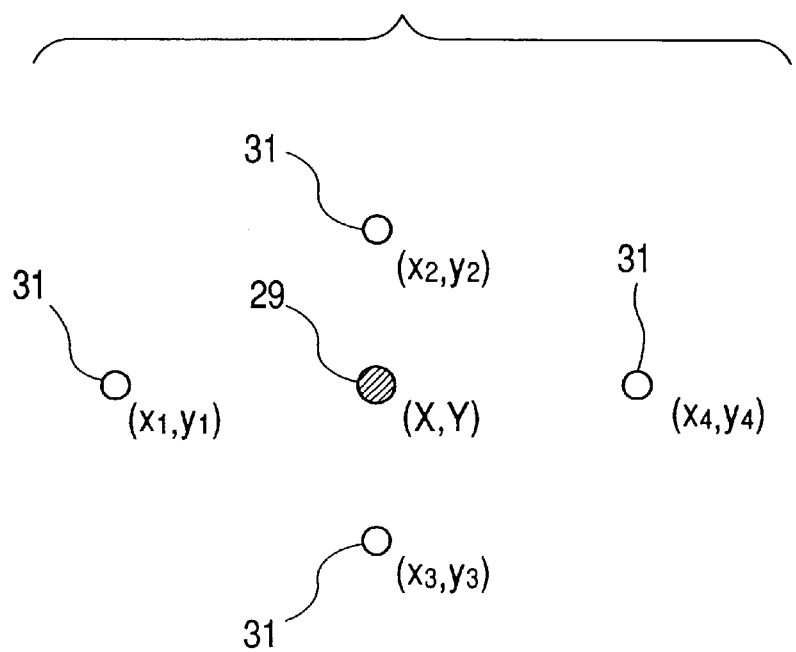
FIG. 3 is a view showing a condition that marks are formed in the vicinity of defect or foreign matter by using the apparatus of FIG. 1.
Figure 4:
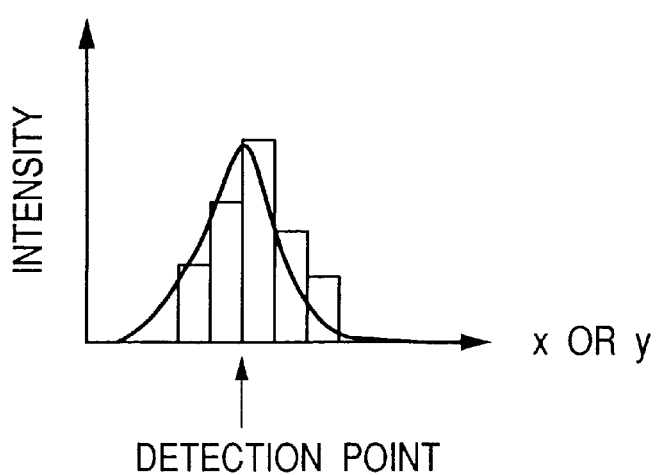
FIG. 4 is a view showing a condition that positions of the defect or foreign matter marks are appropriately determined by using Gauss curves regarding image data of the defect and the like in the apparatus of FIG. 1.

With this arrangement, in order to form a thin specimen (sample) for observing the defect or foreign matter in the test object 3 by means of the TEM, first of all, the observing laser light 1 is illuminated onto the test object 3 and the defect or foreign matter in the illuminated test object 3 is observed, thereby positioning the defect and the like within the visual field of the microscope 5. Then, as shown in FIG. 3, the marks are formed at four points on the test object in the vicinity of the defect or foreign matter 29 while ascertaining the illumination position of the marking laser beam 7 by the illumination of the spot light, and positions $(x_i, y_i)$i=1 to 4 of the four marks 31 obtained by the marking and a position (X, Y) of the defect or foreign matter are detected by the information processing means 21 through the microscope 5. Such detection is performed with accuracy of pixel unit or more by closely approximating intensity distribution of data (unit data of CCD element or the like of the TV camera 19) of each pixel constituting the image data to Gauss distribution (sub-pixel treatment).

Then, the test object 3 is rested on a TEM sample forming tool using FIB (Fine ion beam) or the like, and the positions $(x_i', y_i')$i=1 to 4 of the marks 31 are detected in the manner similar to the above. And, the following coordinate conversion determinant between coordinates (x, y) on the defect observing apparatus and coordinates (x', y') on the TEM sample forming tool is sought on the basis of $(x_i, y_i)$ and $(x_i', y_i')$:

$$\begin{pmatrix} x' \\ y' \end{pmatrix} = \begin{pmatrix} a_{11} & a_{12} \\ a_{21} & a_{22} \end{pmatrix} \begin{pmatrix} x \\ y \end{pmatrix}$$

By using (X, Y), the position (X', Y') of the defect or foreign matter on the TEM sample forming tool is sought, and, the sample including the defect or foreign matter 29 is formed on the basis of this position. The sample is a thin plate having a thickness of several thousand Å obtained by cutting the surface of the test object 3 vertically. By observing the sample through the TEM, information regarding the defect or foreign matter 29, namely, a depth position of the defect or foreign matter 29 from the surface of the test object 3 and/or scattering intensity due to the defect or foreign matter 29 can be observed.

According to this arrangement, the defect or foreign matter can be found through a wide visual field by the laser tomography and identity of the defect or foreign matter can be evaluated by TEM, FIB, SIMS or the like having high resolving power.

As mentioned above, according to the present invention, since the marks representative of the position of the defect or foreign matter under the microscope for observing the defect or foreign matter are provided and the positional relation therebetween is detected through the microscope, the TEM observing specimen can be formed positively and easily.

In comparison with the conventional technique in which an approximate position to be observed by the laser tomography was found by using a laser tomographic observing device and a laser marking device independently and the laser marking was effected in the vicinity of such a position and the position was ascertained by the laser tomography again and the TEM observing specimen was formed by the specimen forming tool using FIB, the TEM observing specimen can be formed more positively and for a shorter time.

Further, since the marking laser beam is directed to the optical axis of the microscope and the marking is effected through the microscope, in comparison with the case where the laser tomographic observing device and the laser marking device independently, the TV camera, the microscope and an electrically-powered stage for shifting the test object can be used in common between the laser tomography and the laser marking, thereby reducing the manufacturing cost.

In addition, since the mark positions and the position of the defect and the like can be detected with higher accuracy than arrangement pitch of pixels by using the sub-pixel treatment, the TEM observing specimen can be formed with accuracy corresponding to the high resolving capability of the TEM and the like.

What is claimed is:

1. A defect observing apparatus used in observation of defect or foreign matter in an object to be tested by means of a laser scattering method and including illumination means for illuminating observing laser light onto the object to be tested, and a microscope for observing the illuminated object to be tested, said apparatus comprising:

marking means for forming marks at a plurality of points on a surface of the object to be tested in the vicinity of the defect or foreign matter to be observed under said microscope, and position detecting means for detecting positions of the plurality of marks formed on the surface of the object to be tested and a position of the observed defect or foreign matter through said microscope.

2. The apparatus according to claim 1, wherein said marking means is adapted to direct a marking laser beam to an optical axis of said microscope and to effect the marking at the plurality of point on the object to be tested, by using the marking laser beam through said microscope.

3. The apparatus according to claim 1, wherein said marking means is adapted to effect the marking at the plurality of points on the object to be tested, by means of a marker of contact probe type, while shifting the object to be tested.

4. The apparatus according to claim 2, further comprising means for illuminating spot light onto an illuminated position through said microscope in order to previously ascertain the illuminated positions, before the marking laser light is illuminated onto the object to be tested in order to form the marks.

5. The apparatus according to claim 4, wherein said means for illuminating the spot light is adapted to direct light flux for forming the spot light to the optical axis of said microscope through a dichroic mirror, and said marking means is adapted to direct the marking laser light to the optical axis of said microscope through said dichroic mirror.

6. A defect observing method comprising:
   a marking step for illuminating observing laser light onto an object to be tested, for seeking defect or foreign matter in the illuminated object to be tested by a microscope and for forming marks at a plurality of points on a surface of the object to be tested in the vicinity of the defect or foreign matter under said microscope;

a position detecting step for detecting positions of the plurality of marks obtained by marking and a position of the observed defect or foreign matter through said microscope;

a specimen forming step for forming a thin specimen including the defect or foreign matter from the object to be tested, on the basis of a positional relation between the marks and the defect or foreign matter obtained from a detected result; and an observing step for obtaining information regarding the defect or foreign matter by observing the thin specimen.

7. The method according to claim 6, wherein, when the mark positions and the position of the defect or foreign matter are detected in said position detecting step, the marks formed by the marking at the plurality of points and the defect or foreign matter are imaged by an imaging means through said microscope, and, the mark positions and the position of the defect or foreign matter are detected with accuracy higher than arrangement pitch of pixels by sub-pixel treatment on the basis of image data obtained by the imaging.

8. The method according to claim 6, wherein, in said specimen forming step, the positions of the marks formed on the object to be tested are detected, and the position of the defect or foreign matter is ascertained on the basis of a positional relation between the marks and the defect or foreign matter, and the thin specimen including the defect or foreign matter is formed.

* * * * *